United States Patent
Xiu et al.

(10) Patent No.: US 9,127,116 B2
(45) Date of Patent: Sep. 8, 2015

(54) FUNCTIONAL SILANE-COMPATIBILIZED EPOXY COMPOSITIONS FOR INSULATION APPLICATIONS

(75) Inventors: Tong Ping T. Xiu, Shanghai (CN); Yong-jiang Li, Shanghai (CN); Hongyu Chen, Shanghai (CN); Yi Zhang, Shanghai (CN); Ming L. Ji, Shanghai (CN)

(73) Assignee: Dow Global Technologies LLC, Midland, MI (US)

(*) Notice: Subject to any disclaimer, the term of this patent is extended or adjusted under 35 U.S.C. 154(b) by 0 days.

(21) Appl. No.: 14/359,386

(22) PCT Filed: Dec. 30, 2011

(86) PCT No.: PCT/CN2011/085080
§ 371 (c)(1),
(2), (4) Date: May 20, 2014

(87) PCT Pub. No.: WO2013/097197
PCT Pub. Date: Jul. 4, 2013

(65) Prior Publication Data
US 2014/0378625 A1 Dec. 25, 2014

(51) Int. Cl.
C08G 77/04 (2006.01)
C08G 59/40 (2006.01)
C07F 7/08 (2006.01)
C08G 59/42 (2006.01)
C08L 63/00 (2006.01)
C08G 59/24 (2006.01)
C08G 77/16 (2006.01)

(52) U.S. Cl.
CPC ............ *C08G 59/4085* (2013.01); *C07F 7/081* (2013.01); *C08G 59/24* (2013.01); *C08G 59/42* (2013.01); *C08L 63/00* (2013.01); *C08G 77/16* (2013.01)

(58) Field of Classification Search
CPC ...... C08G 77/16; C08G 59/42; C07F 7/0814; C07F 7/081
USPC ........................................................ 525/476
See application file for complete search history.

(56) References Cited

U.S. PATENT DOCUMENTS

| 5,212,218 | A  | 5/1993 | Rinehart |
| 5,755,608 | A  | 5/1998 | Glickman |
| 6,048,946 | A  | 4/2000 | Beisele |
| 6,764,616 | B1 | 7/2004 | Beisele et al. |
| 2002/0142167 | A1 | 10/2002 | Yamaguchi et al. |
| 2010/0227158 | A1 | 9/2010 | Clifford et al. |
| 2010/0326699 | A1 | 12/2010 | Greyling |
| 2011/0027532 | A1 | 2/2011 | Schmidt et al. |
| 2012/0111605 | A1 | 5/2012 | Tzavalas et al. |

FOREIGN PATENT DOCUMENTS

| CN | 101117557 A   |   | 2/2008  |
| CN | 102532809 A   |   | 7/2012  |
| JP | 2002 020587   | * | 1/2002  |
| JP | 2002020587 A  |   | 1/2002  |
| SU | 316712        |   | 10/1971 |

OTHER PUBLICATIONS

JP 2002 020587 machine translation (2002).*
Velan, Thanikai, T.V., and Bilal, Mohammed I. "Aliphatic amine cured PDMS—epoxy interpenetrating network system for high performance engineering applications—Development and characterization" Bull. Mater. Sci. Oct. 2000, p. 425-429, 23(5), Indian Academy of Sciences.
Liu Weiqu et al. (Toughening of Epoxy Resin System Using a Novel Dendritic Polysiloxane; Morphologies and mechanical and thermal properties of highly epoxidized polysiloxane toughened epoxy resin composites).
M Suguna Lakshmi and Reddy, BSR., "Development of Inter-Crosslinking Polymer Materials From DGEBA/PDMS Epoxy Resin Systems: Processing and Application Stud", Malaysian Polymer Journal, vol. 5, No. 2, p. 84-98, 2010.
Gonzalez, et al. (Crosslinking of epoxy-polysiloxane system by reactive blending), Polymer, 45 (2004) 5533-5541.
Zhao et al. (Preparation and properties of polydimethylsiloxane-modified epoxy resin) Journal of Applied Polymer Science, vol. 76, 1683-1690 (2000).
Xinsheng, B. et. al. "Preparation and Properties of Epoxy Resin Modified by Liquid Chloroprene-Hydroxyethylemthacrylate copolymer" Polymer Communications, 1985, 300-304.
PCT/CN2011/085080, International Search Report and Written Opinion of the International Searching Authority, Oct. 18, 2012.
PCT/CN2011/085080, International Preliminary Report on Patentability. Jul. 7, 2014.

* cited by examiner

*Primary Examiner* — Kuo-Liang Peng

(57) ABSTRACT

Described is an epoxy composition containing: (a) an epoxy resin containing at least one epoxy group, (b) an anhydride hardener, (c) a hydroxyl-terminated polysiloxane, and (d) a functional silane having at least one functional group selected from the group consisting of an epoxy-reactive group, an anhydride-reactive group, and an epoxy- and anhydride-reactive group. Also describing a crosslinked epoxy composition and a method for preparing thereof.

14 Claims, No Drawings

US 9,127,116 B2

FUNCTIONAL SILANE-COMPATIBILIZED EPOXY COMPOSITIONS FOR INSULATION APPLICATIONS

FIELD

The present application relates to an epoxy composition comprising an epoxy resin, an anhydride hardener, a hydroxyl-terminated polysiloxane, and a functional silane having at least one functional group selected from the group consisting of an epoxy-reactive group, an anhydride-reactive group, and an epoxy- and anhydride-reactive group. The present application also related to a crosslinked epoxy composition and a method for preparing thereof.

BACKGROUND

Casting epoxy compositions are widely used as electrical insulating materials (for example, insulators) due to balanced mechanical and electrical properties, heat and chemical resistance of epoxy resins, compared to incumbent liquid silicone rubber based insulators. However, casting epoxy compositions still have some issues, especially in regions having high levels of precipitation and air pollution. In these regions, a conductive dirt and/or water layer may form on the surface of the insulator, which can lead to current leakage, arcing, and may result in insulator damage or even total failure. To avoid damaging water and water-born contamination on an epoxy composition insulator material, it is desirably that the epoxy compositions have a hydrophobic surface.

To increase hydrophobic surface properties of epoxy compositions, polysiloxanes (for example, hydroxyl-terminated polysiloxanes) owing to their low surface energy, are usually added into epoxy resins. However, since polysiloxanes and epoxy resins are thermodynamically immiscible, simply mixing them usually will not provide satisfactory hydrophobic surface properties. Satisfactory hydrophobic surface properties refer to a surface having a contact angle with deionized water that is 90° or greater.

To increase compatibility between epoxy resins and polysiloxanes, one incumbent solution is to provide a composition comprising a cycloaliphatic epoxy resin, a hydroxyl-terminated (OH-terminated) polysiloxane, a cyclic polysiloxane, and a non-ionic and fluoroaliphatic surface-active reagent. The cured composition obtained has hydrophobicity transfer effect (that is, ability of surfaces to turn hydrophilic pollution into hydrophobic layers) and hydrophobicity recovery effect (that is, ability of surfaces to recover their initial hydrophobic properties after losses resulting, for example, from plasma treatment). However, since the polysiloxane is not chemically built into the network of the cured composition, the OH-terminated polysiloxane and cyclic polysiloxane can be gradually depleted due to migration to the surface, which will result in gradually decreased hydrophobic properties.

Another incumbent approach is synthesizing a siliconized aromatic epoxy interpenetrating polymer network (IPN) by using polyaminoamine as a curing agent and γ-aminopropyltriethoxysilane (γ-APS) as a crosslinking agent for crosslinking diglyceryl ether of bisphenol-A (DGEBA) and OH-terminated polydimethylsiloxane (PDMS). Durability of hydrophobic properties can be imparted to the cured epoxy composition, since PDMS chains are chemically bonded to the network. However, this is an inefficient use of PDMS material because it is evenly distributed throughout the bulk material as opposed to concentrated on the surface. In this case, to increase tracking index of epoxy compositions, large amounts of OH-terminated PDMS are needed, which usually results in decreased tensile and flexural strengths of the cured epoxy composition and is not cost-effective.

Thus, it is desirable to provide an epoxy composition having a surface contact angle with deionized water equal to or greater than 90° (that is, having a hydrophobic surface), resistance to degradation of hydrophobic properties (that is, durable hydrophobic properties), at the same time, without compromising mechanical properties of epoxy compositions. It is also desirable that the hydrophobic surface can be achieved by adding low content of OH-terminated polysiloxane. It is also desirable that an epoxy composition provides hydrophobicity transfer effect and hydrophobicity recovery effect.

BRIEF SUMMARY

The present invention provides an epoxy composition with the aforementioned desirable properties. The present invention uses a specific content of functional silane as a reactive compatibilizer for an OH-terminated polysiloxane and an epoxy resin in combination with an anhydride hardener, which achieves a surprising combination of increased and durable hydrophobic surface properties without compromising mechanical properties of the epoxy composition.

Surprisingly, the invention provides a hydrophobic surface even with low concentration of the OH-terminated polysiloxane. For example, the present invention can provide a crosslinked epoxy composition having a surface contact angle with deionized water as high as 108° with only one weight percent of OH-terminated polysiloxane based on the weight of the epoxy resin. Thus, the invention is also cost-effective. The polysiloxane chemically bonded into the network of the crosslinked epoxy composition imparts the crosslinked epoxy composition durable hydrophobic surface. The crosslinked epoxy composition has sufficient tracking resistance to pass 1A3.5 (according to IEC 60587 testing method). In addition, the invention further provides hydrophobicity transfer effect and hydrophobic recovery effect.

In a first aspect, the invention is an epoxy composition comprising:
(a) an epoxy resin containing at least one epoxy group,
(b) an anhydride hardener,
(c) a hydroxyl-terminated polysiloxane, and
(d) a functional silane having at least one functional group selected from the group consisting of an epoxy-reactive group, an anhydride-reactive group, and an epoxy- and anhydride-reactive group, wherein molar ratio of the epoxy-reactive group or the epoxy- and anhydride-reactive group to the epoxy group is less than 0.25;
wherein molar ratio of total hydroxyl group(s) in the hydroxyl-terminated polysiloxane to total alkoxy group(s) in the functional silane is 3.5 or less.

In a second aspect, the invention is a crosslinked epoxy composition made by curing the epoxy composition of the first aspect.

In a third aspect, the invention is a method for preparing the crosslinked epoxy composition of the second aspect, comprising steps of mixing a functional silane, a hydroxyl-terminated polysiloxane, a cycloaliphatic epoxy resin and an anhydride hardener.

DETAILED DESCRIPTION

Test methods refer to the most recent test method as of the priority date of this document when a date is not indicated with the test method number. References to test methods contain both a reference to the testing society and the test method number. The following test method abbreviations and identifiers apply herein: ASTM refers to American Society for Testing and Materials; IEC refers to International Electrotechinical Commission; and ISO refers to International Organization for Standards.

"And/or" means "and, or as an alternative". All ranges include endpoints unless otherwise indicated.

An epoxy resin is any compound containing at least one or more reactive oxirane groups (—$C_2H_3O$), referred to herein as "epoxy group(s)" or "epoxy functionality". Epoxy resins may include mono-functional epoxy resins, multi- or polyfunctional epoxy resins, and combinations thereof. The polymeric epoxies include linear polymers having terminal epoxy groups (for example, a diglycidyl ether of a polyoxyalkylene glycol), polymer skeletal oxirane units (for example, polybutadiene polyepoxide) and polymers having pendant epoxy groups (for example, a glycidyl methacrylate polymer or copolymer). The epoxy resins may be pure compounds, but are generally mixtures or compounds containing one, two or more epoxy groups per molecule. The epoxy resin may be saturated or unsaturated, aliphatic, cycloaliphatic, aromatic or heterocyclic and may be substituted. The epoxy resin may also be monomeric or polymeric. The epoxy resins may include, for example, cycloaliphatic epoxy resins, cycloaliphatic epoxy resins modified with glycols, epoxy phenolic novolac resins and cresol novolac type epoxy resins, multifunctional (polyepoxy) epoxy resins, bisphenol A-based epoxy resins, bisphenol F-based epoxy resins, and mixtures thereof.

To increase resistance to weathering for outdoor use, the epoxy resin preferably comprises a cycloaliphatic epoxy resin. A cycloaliphatic epoxy resin according to the present invention is a hydrocarbon compound containing at least one non-aryl hydrocarbon ring structure and containing an epoxy group. The epoxy group in the cycloaliphatic epoxy compound may include an epoxy group fused to the ring structure and/or an epoxy group residing on an aliphatic substituent of the ring structure. Preferably, the cycloaliphatic epoxy compound has at least one epoxy group residing on an aliphatic substituent of the ring. The cycloaliphatic epoxy resin may be a monoepoxide compound. Preferably, the cycloaliphatic epoxy resin has two or more epoxy groups. The cycloaliphatic, epoxy resin may include cycloaliphatic epoxides modified with glycols.

Preferably, the cycloaliphatic epoxy resin has an epoxy group fused to the non-aryl hydrocarbon ring structure, which is a saturated carbon ring having an epoxy oxygen bonded to two vicinal atoms in the carbon ring, as illustrated by the following structure (I):

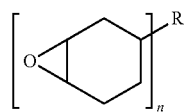

(I)

wherein R is an aliphatic, cycloaliphatic and/or aromatic group and n is a number from one to 10, preferably from 2 to 4. When n is one, the cycloaliphatic epoxy resin is a monoepoxide. Di- or epoxy resins are formed when n is two or more. Mixtures of mono-, di- and/or epoxy resins may be used. Cycloaliphatic epoxy resins as described in U.S. Pat. No. 3,686,359, may be used in the invention.

Examples of suitable cycloaliphatic epoxy resins include, diepoxides of cycloaliphatic esters of dicarboxylic acids, such as bis(3,4-epoxycyclohexylmethyl)oxalate; bis(3,4-epoxycyclohexylmethyl)adipate; bis(3,4-epoxy-6-methylcyclohexylmethyl)adipate; bis(3,4-epoxycyclohexylmethyl) pimelate; vinylcyclohexene diepoxide; 3,4-epoxycyclohexylmethyl-3,4-epoxycyclohexane carboxylate; limonene diepoxide; bis[(3,4-epoxycyclohexyl)methyl]dicarboxylates; bis[(3,4-epoxy-6-methylcyclohexyl)methyl] dicarboxylates; glycidyl 2,3-epoxycyclopentyl ether; cyclopentenyl ether diepoxide; 2,3-epoxycyclopentyl-9,10-epoxystearate; 4,5-epoxytetrahydrophthalic acid diglycidyl ester; bis(2,3-epoxycyclopentyl)ether; 2-(3,4-epoxycyclohexyl)-5,5-spiro(2,3-epoxycyclohexane)-m-dioxane; 2-(3,4-epoxycyclohexyl)-5,5-spiro(3,4-epoxy cyclohexane)-m-dioxane; (3,4-epoxy-6-methylcyclohexyl)methyl 3,4-epoxy-6-methylcyclohexane and 1,2-bis(2,3-epoxycyclopentyl) ethane and dicyclopentadiene diepoxide. Other suitable diepoxides of cycloaliphatic esters of dicarboxylic acids are described, for example, in U.S. Pat. No. 2,750,395. Commercially available cycloaliphatic epoxy resins include ERL™, D.E.R.™ or D.E.N.™ epoxy resins (ERL, D.E.R. and D.E.N. are trademarks of The Dow Chemical Company), all available from The Dow Chemical Company. Also, CELLOXIDE™ 2021 (CELLOXIDE is a trademark of Daicel Chemical Industries), CELLOXIDE 2021P, EPOLEAD GT301, and CELLOXIDE 2080 series are cycloaliphatic epoxy resins commercially available from Daicel Chemical Industries.

Examples of other suitable cycloaliphatic epoxy resins include a reaction product of epichlorohydrin or glycerol dichlorohydrin or β-methylepichlorohydrin with cycloaliphatic alcohols or cycloaliphatic polycarboxylic acids, such as 1,2-cyclohexanedicarboxylic acid diglycidyl ester, bis(4-hydroxycylohexyl)methanediglycidyl ether, tetraydrophthalic acid diglycidyl ester, 4-methylhexahydrophthalic acid diglycidyl ester, hexahydrophthalic acid diglycidyl ester; or 2,2-bis(4-hydroxycyclohexyl)propane diglycidyl ether and mixtures thereof. Preferably, the cycloaliphatic epoxy resins include 1,2-cyclohexanedicarboxylic acid diglycidyl ester or 2,2-bis(4-hydroxycyclohexyl)propane diglycidyl ether. Methods for producing a variety of useful cycloaliphatic epoxy resins are known to those skilled in the art.

The amount of the epoxy resin in the epoxy composition is desirably one weight percent (wt %) or more, preferably 5 wt % or more, more preferably 10 wt % or more, still most preferably 15 wt % or more and at the same time desirably 95 wt % or less, preferably 70 wt % or less, more preferably 60 wt % or less and still most preferably 50 wt % or less, based upon the total weight of the epoxy composition.

The epoxy composition of the invention further comprises a hydroxyl-terminated polysiloxane. The hydroxyl-terminated polysiloxane herein refers to a polysiloxane with at least one or more hydroxyl end groups. The polysiloxane containing hydroxyl end group(s) useful in the invention may comprise from 2 to 100,000 or more units of the formula

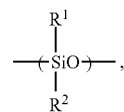

in which $R^1$ and $R^2$ are independently selected from a group consisting of substituted or unsubstituted alkyl groups comprising one to 18 carbon atoms, substituted or unsubstituted alkenyl groups comprising two to 14 carbon atoms, substituted or unsubstituted aryl groups comprising 5 to 14 carbon atoms, fluorine substituted alkyl groups comprising one to 14 carbon atoms, and substituted or unsubstituted aralkyl groups comprising 6 to 24 carbon atoms. The $R^1$ or $R^2$ groups can be, for example, methyl, ethyl, n-propyl, isopropyl, n-butyl, sec-butyl, dodecyl, vinyl, allyl, phenyl, naphthyl, tolyl, 3,3,3-trifluoropropyl, benzyl, or phenylethyl. Preferably, $R^1$ and $R^2$ are independently methyl, ethyl, propyl or phenyl. More preferably, $R^1$ and $R^2$ are independently methyl or ethyl.

Preferably, the hydroxyl-terminated polysiloxane contains two or more hydroxyl end groups, such as a hydroxyl-terminated polydimethylsiloxane containing at least two hydroxyl end groups. In preferred embodiments, the polydimethylsiloxane is of the formula (II),

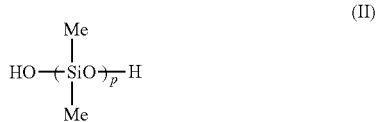

(II)

in which Me is methyl and p is in the range of one to 100,000 or more. The value "p" can have a lower limit of one, or 2, or 3, or 4, or 5, or 10, or 15, or 20 and an upper limit of 50, or 75, or 100, or 120, or 400, or 1000, or 100,000. Examples of commercially available hydroxyl-terminated polysiloxanes include DMS-S15 from Gelest, Inc.

Molecular weight of the OH-terminated polysiloxane is desirably 400 grams per mole (g/mol) or more, preferably 1000 g/mol or more, more preferably 1400 g/mol or more, at the same time desirably 150,000 g/mol or less, preferably 80,000 g/mol or less and more preferably 70,000 g/mol or less.

The weight ratio of the OH-terminated polysiloxane to the epoxy resin is desirably 0.1% or more, preferably 0.5% or more and more preferably 1% or more. To be cost-effective or to achieve balanced mechanical properties, the weight ratio of the OH-terminated polysiloxane to the epoxy resin is desirably 30% or less, preferably 25% or less, more preferably 20% or less, most preferably 10% or less, and still most preferably 5% or less.

The epoxy composition of the invention also comprises a functional silane having at least one functional group selected from the group consisting of an epoxy-reactive group, an anhydride-reactive group, and an epoxy- and anhydride-reactive group. "Epoxy-reactive" group refers to any group able to react with an epoxy group. "Anhydride-reactive" group refers to any group able to react with an anhydride group. "Epoxy- and anhydride-reactive" group refers to any group able to react with both an epoxy group and an anhydride group. The functional silane herein refers to a silane having at least one functional group, which is able to react with an epoxy or an anhydride group, or able to react with both an epoxy group and an anhydride group.

A preferred functional silane is represented by general formula (III):

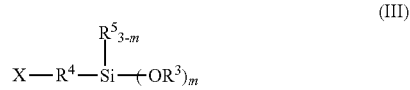

(III)

where $R^3$ represents an alkyl group having one to 6 carbon atoms; $OR^3$ group represents an alkoxy group including, for example, methoxy, ethoxy or acetoxy group; $R^4$ represents a bivalent organic group having a molecular weight of 200 or less; $R^5$ represents a hydrogen atom or an alkyl, aryl, or aralkyl group having one to 20 carbon atoms; X represents a functional group selected from the group consisting of an epoxy-reactive group, an anhydride-reactive group, and an epoxy- and anhydride-reactive group; and m is one, 2 or 3. $R^4$ group may have a side chain. Preferably, $R^4$ group further comprises one, two or more epoxy-reactive, anhydride-reactive, or epoxy- and anhydride-reactive functionality.

Examples of suitable functional silanes include an aminosilane, an epoxy silane, an anhydride functional silane, an isocyanate functional silane, or a sulfhydryl functional silane. Preferably, the functional silanes include an aminosilane or an epoxy silane.

To provide a hydrophobic surface, molar ratio of total hydroxyl group(s) in the hydroxyl-terminated polysiloxane to total alkoxy group(s) in the functional silane is 3.5 or less, desirably 3.4 or less, preferably 3.0 or less, more preferably 2.5 or less, most preferably 1.5 or less and still most preferably 1.2 or less. If the molar ratio is greater than 3.5, the polysiloxane chains cannot be effectively built into the network of cured epoxy compositions; therefore, the cured epoxy compositions are difficult to afford satisfactory hydrophobic surface proprieties. Preferably, the molar ratio is desirably 0.001 or more, preferably 0.003 or more, more preferably 0.005 or more, most preferably 0.006 or more and still most preferably 0.01 or more.

In addition, when the functional group is an epoxy-reactive group or an epoxy- and anhydride-reactive group, the functional silane should be in an amount to minimize crosslinking of the epoxy resin. In this case, if the content of the functional silane is too high, the viscosity of the epoxy composition is too high and the epoxy composition is difficult to be processed. Molar ratio of the epoxy-reactive group or the epoxy- and anhydride-reactive group in the functional silane to the epoxy group(s) in the epoxy resin is less than 0.25, preferably 0.2 or less, more preferably 0.1 or less.

The epoxy composition of the invention preferably comprises an aminosilane. An aminosilane means a silane having at least one primary or secondary amine functionality. A preferred aminosilane compound is represented by general formula (IV)

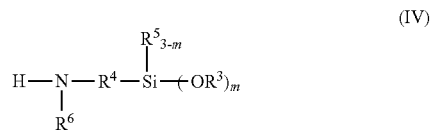

(IV)

where $R^6$ represents a hydrogen atom, a phenyl group, or a substituted or unsubstituted organic group having one to 20 carbon atoms; $R^3$, $R^4$, $R^5$, m are the same as those described above. The amine functionality of the aminosilane may be one, 2, 3 or more. The aminosilane compound may be used alone or in combination of two or more.

Examples of suitable aminosilane compounds include γ-aminopropylmethyldimethoxysilane, γ-aminopropylmethyldiethoxysilane, γ-aminopropyltrimethoxysilane, γ-aminopropyltriethoxysilane, γ-aminophenyltrimethoxysilane, aminoethylaminopropyltrimethoxysilane, aminoethylaminopropyltriethoxysilane, aminoethylaminoethylaminopropyltrimethoxysilane, aminoethylaminomethylmethyldiethoxysilane, (3-aminopropyl)-diethoxy-methylsilane, (3-aminopropyl)-dimethyl-ethoxysilane, (3-aminopropyl)-trimethoxysilane, N-(β-aminoethyl)-γ- aminopropyltriethoxysilane, γ-aminopropyldimethylmethoxysilane, N-(β-aminoethyl)-γ-aminopropyltrimethoxysilane, N-phenyl-γ-aminopropyltrimethoxysilane, (aminoethylaminomethyl)phenethyltrimethoxysilane, N-(β-aminoethyl)-γ-aminopropylmethyldimethoxysilane, N-(6-aminohexyl)-3-aminopropyltrimethoxysilane, N-(2-aminoethyl)-11-aminoundecyltrimethoxysilane, N-(β-aminoethyl)-γ-aminopropylethyldiethoxylsilane, and mixtures thereof.

The epoxy composition of the invention preferably comprises an epoxy silane. An epoxy silane means a functional silane having at least one epoxy group. A preferred epoxy silane has the general formula (V):

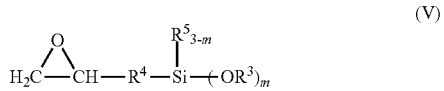

(V)

where $R^3$, $R^4$, $R^5$, m are the same as those described above.

Examples of suitable epoxy silane compounds include 3-glycidyloxypropyl trimethoxysilane, 3-glycidyloxypropyl triethoxysilane, 3-glycidyloxypropyl methyldiethoxysilane, 3-glycidyloxypropyl methyldimethoxysilane, 2-(3,4-epoxy-cyclohexyl)-ethyltrimethoxysilane, and mixtures thereof.

The epoxy composition of the invention also comprises an anhydride hardener. An anhydride hardener contains an anhydride functional group, which reacts with oxirane groups to form a bond thereto and extend the polymer chain. Anhydride hardeners may also include copolymers of styrene and maleic acid anhydrides and other anhydrides as described in U.S. Pat. No. 6,613,839. Preferably, the epoxy composition of the invention may include one or more cycloaliphatic anhydride hardeners.

Examples of suitable cycloaliphatic anhydride hardeners include, nadic methyl anhydride, hexahydrophthalic anhydride, trimellitic anhydride, dodecenyl succinic anhydride, phthalic anhydride, methyl hexahydrophthalic anhydride, tetrahydrophthalic anhydride, methyl tetrahydrophthalic anhydride, succinic anhydride, ciraconic anhydride, itaconic anhydride, alkenyl-substituted succinic anhydride, maleic anhydride, tricarballylic anhydride, a maleic adduct with cyclopentadiene or methylcyclopentadiene, a linoleic acid adduct with maleic anhydride, alkylated endoalkylenetetrahydrophthalic anhydrides, and mixtures thereof.

The anhydride hardener is used in sufficient amount to cure the epoxy composition. Molar ratio of total anhydride group(s) in the epoxy composition to total epoxy group(s) in the epoxy composition is desirably 0.4 or more, preferably 0.8 or more and at the same time is desirably 1.6 or less and preferably 1.2 or less.

The epoxy composition may optionally comprise a curing catalyst. A curing catalyst is a catalyst that accelerates a curing reaction between the epoxy resin and an epoxy-reactive compound (for example, hardeners). Examples of suitable curing catalysts include benzyldimethylamine (BDMA), 1-methylimidazole (1-MI) and mixtures thereof. The weight content of the curing catalyst is desirably 0.01% or more, preferably 0.1% or more, at the same time is desirably 5% or less and preferably 1% or less, based on the weight of the epoxy resin.

The epoxy composition may optionally comprise a condensation catalyst. The condensation catalyst is to accelerate a condensation reaction between the hydroxyl group(s) in the OH-terminated polysiloxane and the alkoxy group(s) in the functional silane. The condensation catalyst is an organometallic compound. Metal portion of the organometallic compound may vary from manganese to lead in the Periodic Table. Preferably, an organotin compound is used. Examples of suitable organometallic compounds include dibutyltin dilaurate, dibutyl tin oxide, tin octoate and mixtures thereof. The epoxy composition desirably comprises from 0.1 to 5 wt % of the condensation catalyst, based on the total weight of the OH-terminated polysiloxane and the functional silane.

The epoxy composition may further comprise a cyclic polysiloxane to impart cured epoxy compositions with increased hydrophobicity recovery effect and hydrophobicity transfer effect. The hydrophobicity recovery effect means an ability of surfaces to recover their initial hydrophobic properties after losses resulting, for example, from plasma treatment. The hydrophobicity transfer effect means an ability of surfaces to turn hydrophilic pollution into hydrophobic layers.

A preferred cyclic polysiloxane has a general formula (VI)

(VI)

$R^1$, $R^2$ are the same as those described above; and q is an integer from 3 to 12. Preferably, q is from 4 to 8 and more preferably from 4 to 6. Preferably, $R^1$, $R^2$ is independently methyl, ethyl, propyl or phenyl, more preferably is methyl.

Examples of suitable cyclic polysiloxane compounds include octamethylcyclotetrasiloxane, decamethylcyclopentasiloxane, tetraoctyl cyclotetrasiloxane, hexamethylcyclotrisiloxane, dodecamethyl-cyclohexasiloxane, tetra- and penta-methylcyclopentasiloxanes; tetra-, penta- and hexamethyl cyclohexasiloxanes, tetraethyl cyclotetrasiloxane, tetraphenyl cyclotetrasiloxanes, and mixtures thereof. Preferably, the cyclic polysiloxane is decamethylcyclopentasiloxane, which is commercially available.

The content of the cyclic polysiloxane is desirably 0.01% by weight or more, preferably 0.1% by weight or more, more preferably 1% by weight or more, at the same time is desirably 10% by weight or less, preferably 5% by weight or less and more preferably 3% by weight or less, based on the weight of the epoxy resin.

The epoxy composition may optionally comprise fillers. Examples of suitable fillers include silicone oxide (for example, quart sand, quartz powder, silanized quartz powder, fused silica powder, silanized fused silica powder), aluminum oxide, titanium oxide, metal hydroxides (for example, $Al(OH)_3$, $Mg(OH)_2$), semi-metal and metal nitrides, semi-metal and metal carbides, and mixtures thereof. The content of the fillers is desirably 20% by weight or more, preferably 50% by weight or more, at the same time is desirably 80% by weight or less, preferably 70% by weight or less, based on the total weight of the epoxy composition.

The epoxy composition can include, or be free from, any one or combination of more than one of the following auxiliary components: antioxidants, light stabilizers, antioxidants, flame retardants (for example, inorganic flame retardants, halogenated flame retardants, and non-halogenated flame retardants such as phosphorus-containing materials), plasticizers, dyes, colorants or pigments, fungicides, thixotropic agents, toughening agents, processing aids, impact modifiers including thermoplastic particles, antifoaming agents, antistatic agents, lubricants, anti-settling agents, wetting agents, mould-release agents, surfactants, flow modifiers, matting agents, degassing agents, curing initiators, curing inhibitors, fluorescent compounds, UV stabilizers, fibrous reinforcements, and mixture thereof. The amount of the auxiliary components in the epoxy composition is known to those skilled in the art. For example, the epoxy composition may comprise the auxiliary components in an amount of 0.01% by weight or more, preferably 0.1% by weight or more and at the same time 5% by weight or less and preferably 2% by weight or less, based on the total weight of the epoxy composition.

The epoxy composition is desirably formed by admixing the epoxy resin, OH-terminated polysiloxane, functional silane, anhydride hardener, and optionally, catalysts, cyclic polysiloxane, fillers and auxiliary components in any convenient order.

The epoxy composition of the present invention can be cured to form a crosslinked epoxy composition. The crosslinked epoxy composition has surprisingly satisfactory hydrophobic surface properties. An epoxy composition having satisfactory hydrophobic surface properties gives a surface contact angle with deionized water of at least 90°. Therefore, hydrophobic properties can also be assessed by measuring surface contact angle with deionized water. Larger surface contact angle with deionized water indicates greater (better) hydrophobic surface properties and, conversely, poorer hydrophobic surface properties are indicated by lower surface contact angle with deionized water.

For determining hydrophobic properties, measure surface contact angle with deionized water using an OCA 20 contact angle instrument from dataphysics or equivalent contact angle instrument. Before the measurement, surface of each sample is cleaned using acetone. A drop of deionized water is placed onto the surface and photographed after equilibrium, then a surface contact angle with deionized water is calculated.

The crosslinked epoxy composition of the invention has a surface contact angle with deionized water of 90° or higher, preferably 95° or higher, more preferably 100° or higher and most preferably 105° or higher. The crosslinked epoxy composition having satisfactory hydrophobic surface properties affords sufficient tracking resistance to pass 1A3.5 (according to IEC 60587 testing method). In addition, mechanical properties (for example, tensile strength and flexural strength) of the crosslinked epoxy composition are not compromised.

Without intending to be limited by theory, the satisfactory hydrophobic surface properties of the invention may be attributed by polysiloxane chains chemically built into the network of the crosslinked epoxy composition, in combination with gradient silicone distribution (that is, more silicones are present on the surface than in the bulk as measured by element mapping using energy dispersive X-ray spectrometer (EDX)) in the crosslinked epoxy composition. Hydroxyl group(s) in the OH-terminated polysiloxane reacts with alkoxy group(s) in the functional silane by the condensation reaction. In addition, the functional group(s) in the functional silane reacts with the epoxy resin or the anhydride hardener. Thus, the polysiloxane chains are chemically bonded into the network of the crosslinked epoxy composition. The anhydride hardener provides relatively slow curing of the epoxy composition compared to that of conventional amine hardeners. Therefore, the polysiloxane chains of low surface energy may have more time to move to the surface while still being chemically bonded into the network of the crosslinked epoxy composition. The combination also contributes to the surprisingly satisfactory hydrophobic surface properties of the epoxy composition with low concentration of the OH-terminated polysiloxane. For example, weight ratio of the OH-terminated polysiloxane to the epoxy resin may be desirably as low as 15% or less, preferably as low as 10% or less, and more, preferably as low as 5% or less.

A method for preparing the crosslinked epoxy composition comprises steps of mixing an epoxy resin containing at least one epoxy group, a functional silane having at least one functional group selected from the group consisting of an epoxy-reactive group, an anhydride-reactive group, and an epoxy- and anhydride-reactive group, a hydroxyl-terminated polysiloxane, an anhydride hardener and optionally other components. Mixing the above components can be carried out in any order. The method may be carried out in one step or in multi-steps, preferably in multi-steps.

For example, the epoxy resin, the hydroxyl-terminated polysiloxane and the functional silane may be mixed to react first, before mixing with the anhydride hardener. Preferably, the functional silane having at least one epoxy-reactive group or at least one epoxy- and anhydride-reactive group reacts with the epoxy resin first.

For example, the anhydride hardener, the hydroxyl-terminated polysiloxane and the functional silane may be mixed to react first, before mixing with the epoxy resin. Preferably, the functional silane having at least one anhydride-reactive group reacts with the anhydride hardener first.

Preferably, the functional silane having at least one epoxy-reactive group or at least one epoxy- and anhydride-reactive group mixes with the epoxy resin and the hydroxyl-terminated polysiloxane together to react first, then the anhydride hardener is added, finally the epoxy composition is cured. More preferably, the functional silane having at least one epoxy-reactive group or at least one epoxy- and anhydride-reactive group mixes with the epoxy resin to react first, and then mixes with the hydroxyl-terminated polysiloxane, followed by adding the anhydride hardener, and finally the epoxy composition is cured. In addition, a curing catalyst may be added into the reaction between the epoxy resin and the functional silane having at least one epoxy-reactive group or at least one epoxy- and anhydride-reactive group.

Preferably, the functional silane having at least one anhydride-reactive group mixes with the epoxy resin and the hydroxyl-terminated polysiloxane to react first, then the anhydride hardener is added, and finally the epoxy composition is cured. It is also desirable that the functional silane having at least one anhydride-reactive group mixes with the anhydride hardener to react first, then reacts with the OH-terminated polysiloxane, further blends with the epoxy resin, optionally, additional anhydride hardener may be added, and finally the epoxy composition is cured.

Conditions for all the above reactions are known to those skilled in the art. The hydroxyl-terminated polysiloxane reacts with the functional silane by the condensation reaction of hydroxyl group(s) and alkoxy group(s). For example, temperature for the condensation reaction is desirably 25 degree centigrade (° C.) or higher, preferably 30° C. or higher, more preferably 60° C. or higher, at the same time is desirably 150° C. or lower, preferably 120° C. or lower; reaction time for the condensation reaction is desirably 15 minutes or more, preferably 30 minutes or more, at the same time is desirably 120 minutes or less and preferably 90 minutes or less. Preferably, a condensation catalyst may be added during or prior to the condensation reaction to accelerate the condensation reaction. Examples of the condensation catalysts are those described as above.

Finally, the epoxy composition is cured to form the crosslinked epoxy composition. Preferably, a curing catalyst may be added to accelerate the curing reaction. The total amount of the curing catalyst includes those added into the reaction between the epoxy resin and the functional silane having at least one epoxy-reactive group or at least one epoxy- and anhydride-reactive group, and/or those added into the curing reaction.

The curing reaction may be carried out, for example, under a temperature of desirably 0° C. or higher, preferably 20° C. or higher, more preferably 60° C. or higher and most preferably 80° C. or higher, at the same time desirably 300° C. or lower, preferably 250° C. or lower, more preferably 200° C. or lower and most preferably 180° C. or lower.

The curing reaction may be carried out, for example, at a pressure of desirably 0.01 bar or higher, preferably 0.1 bar or higher, more preferably 0.5 bar or higher and at the same time desirably 1000 bar or lower, preferably 100 bar or lower, and more preferably 10 bar or lower.

The curing reaction may be carried out for a predetermined period of time sufficient to cure the epoxy composition. For example, the curing time may be desirably one minute or more, preferably 10 minutes or more, more preferably between 100 minutes or more and at the same time may be desirably 24 hours or less, preferably 12 hours or less and more preferably 8 hours or less.

The curing reaction may be a batch or a continuous process. The process may be performed by gravity casting, vacuum casting, automatic pressure gelation (APG), vacuum pressure gelation (VPG), infusion, filament winding, injection (for example, lay up injection), transfer molding, prepreging, dipping, coating, potting, encapsulation, spraying and brushing.

The crosslinked epoxy composition may be used for applications including, for example; insulation (especially outdoor insulation), encapsulation and composites.

EXAMPLES

The following examples illustrate embodiments of the present invention. All parts and percentages are by weight unless otherwise indicated.

EPOTEC YDH 3000 cycloaliphatic epoxy is hydrogenated diglycidyl ether of bisphenol A having equivalent weight of 234, available from Aditya Birla Chemicals (Thailand) Ltd.

EPOTEC YDH 184 cycloaliphatic epoxy is 1,2-cyclohexanedicarboxylic acid diglycidyl ester having equivalent weight of 185, available from Aditya Birla Chemicals (Thailand) Ltd.

Hydroxyl-terminated polydimethylsiloxanes (OH-terminated PDMS) with different molecular weight (MW) (1600 g/mol, 4200 g/mol, 63,000 g/mol), are available from Alfa Aesar.

KH 550 aminosilane is 3-aminopropyl-triethoxysilane (γ-APS) available from TCI.

KH 560 epoxy functional silane is 3-glycidyloxypropyl trimethoxysilane available from TCI.

Methylhexahydrophthalic anhydride (MHHPA) is a hardener available from Polynt Chemical.

Benzyldimethylamine (BDMA) is curing catalyst available from Jiang Du Da Jiang.

W12 EST is quartz powder pretreated with epoxy silane available from Quarzwerke Frechen.

Dibutyltin dilaurate ($C_{32}H_{64}O_4Sn$) is an organometallic compound catalyst available from Aldrich.

Decamethylcyclopentasiloxane is available from TCI.

Surface contact angle with deionized water is measured using an OCA 20 contact angle instrument. Before the measurement, surface of each specimen is cleaned using acetone. A drop of deionized water is placed onto the surface and photographed after equilibrium to obtain the surface contact angle. Larger surface contact angles correspond to greater (better) hydrophobic surface properties.

Glass transition temperature ($T_g$) is measured using a Q-2000 differential scanning calorimeter (DSC) from TA Instruments. Around 8-10 mg of specimen is placed into a T-zero pan. Three scans are applied for each specimen. First scan is to eliminate thermal history in curing process. Third scan is to make sure specimen fully cured. The first scan is from 30° C. to 180° C. at a scan rate of 20 degree centigrade per minute (° C./min). The second and third scans are both from 30° C. to 230° C. at a scan rate of 10° C./min. The instrument is purged using nitrogen gas. $T_g$ is measured during the second scan.

Thermogravimetric analysis (TGA) is performed via a TA Instrument model Q50 TGA with a purge nitrogen gas flow rate of 60 milliliter per minute (ml/min). A specimen is heated from room temperature to 850° C. at a heating rate of 20° C./min. Decomposition temperature ($T_d$) measured is the temperature when the specimen has 5% weight loss.

Tensile tests are performed using dog-bone shape, type I, tensile bars according to ASTM D638. The test is conducted at 25° C. with a crosshead moving speed of 5 millimeter per minute (mm/min) on an Instron 5566 machine.

Three point bending flexural tests are conducted using an Instron 5566 machine with a 10 kiloNewton (kN) load cell. According to ASTM D790, specimen dimensions are 127 millimeter (mm) long, 12.7 mm wide, and 4 mm thick. Tests are conducted at 25° C. with a crosshead moving speed of 1.7 mm/min.

Tracking resistance and erosion resistance are tested according to IEC 60587 testing method. For each sample, five specimens with a dimension of 120 mm*50 mm*6 mm are mounted on a flat test surface. Voltage of 3.5 kiloVoltage (kV) is constantly applied to the specimens for 6 hours. If none of the five specimens shows current exceeding 60 milliAmpere (mA) and no hole is observed, the sample passes 1A3.5 test.

Electric breakdown strength is measured according to the ASTM D149.

Arcing resistance is measured according to IEC 61612. Specimens of 4 mm thickness are used.

Surface resistance and volume resistivity at 25° C. are measured according to IEC 60093 testing method.

Water uptake performance is measured by putting a specimen of 4 mm*50 mm*50 mm in water at 23° C. for 10 days according to ISO 62.

In an Energy-dispersive X-ray spectroscopy (EDX) analysis, a specimen of 4 mm thickness is used. The analysis is conducted on a cross-section area of 2 mm*2 mm. X-rays are generated by high energy electron beam. Electron accelerating voltage is 20 KV. Characteristic X-rays are recorded by a Bruker Quantax-800 X-ray detector.

Example (Ex) 1

Based on the formulations shown in Table 1 (wt % values are relative to total formulation weight), YDH 3000, OH-terminated PDMS and aminosilane are firstly mixed at 80° C. for one hour in presence of dibutyltin dilaurate. Then MHHPA, BDMA and W12 EST are added and mechanically stirred to form a mixture. The mixture is degassed in a vacuum oven at 80° C. until no bubble is observed. A varnish obtained is then casted into a mold and cured in the oven according to the following procedure: 2 hours at 100° C., then 2 hours at 120° C., and finally 2 hours at 160° C.

Example 2

Based on formulations shown in Table 1, epoxy composition of Ex 2 is prepared as in Example 1 except that W12 EST fillers are not added.

Comparative Example A (Comp Ex A)

Based on formulations shown in Table 1, Comp Ex A epoxy composition is prepared. All the components are blended and mechanically stirred at room temperature to form a mixture. The mixture is degassed at a vacuum oven at 80° C. until no bubble is observed. A varnish obtained is then casted into a mold and cured in the oven according to the following procedure: 2 hours at 100° C., then 2 hours at 120° C., and finally 2 hours at 160° C.

TABLE 1

| Raw materials | Ex 1 | Ex 2 | Comp Ex A |
|---|---|---|---|
| YDH 3000, wt % | 23.33 | 58.325 | 23.33 |
| MHHPA, wt % | 15.82 | 39.55 | 15.83 |
| BDMA, wt % | 0.12 | 0.3 | 0.12 |
| OH-terminated PDMS (MW = 4200 g/mol), wt % | 0.7 | 1.75 | 0.72 |
| KH 550, wt % | 0.025 | 0.0625 | N/A |
| Dibutyltin Dilaurate, wt % | 0.005 | 0.0125 | N/A |
| W12 EST, wt % | 60 | N/A | 60 |
| Total, wt % | 100 | 100 | 100 |
| Weight ratio (OH-terminated PDMS/Epoxy resin) | 3% | 3% | 3% |
| Molar ratio (—OH/alkoxy group) | 1 | 1 | N/A |

Surface contact angle with deionized water of the cured epoxy composition of Ex 1 is 110°, showing that the surface is hydrophobic. In addition, the cured epoxy composition has a smooth surface with no flowing oil, suggesting that the aminosilane effectively improves the compatibility between the epoxy resin and the PDMS. The cured epoxy composition of Ex 1 robustly passes 1A3.5 test according to IEC 60587.

Surface contact angle with deionized water of the cured epoxy composition of Ex 2 is 110°. As measured by EDX analysis, silicon atoms are presented more on the surface than in the bulk of the cured epoxy composition of Ex 2, which efficiently impart the surface with hydrophobicity.

In contrast, flowing oil is observed on the surface of the cured epoxy composition of Comp Ex A, which indicates very poor compatibility between the epoxy resin and the OH-terminated PDMS. After cleaning the surface by acetone, surface contact angle with deionized water of the cured epoxy composition of Comp Ex A is only 84° (similar to that of cured pure epoxy resin), which indicates the OH-terminated PDMS almost completely migrates out of the cured epoxy composition.

Examples (Exs) 3-10

Based on formulations shown in Table 2 (wt % values are relative to total formulation weight), YDH 184 and aminosilane are first reacted at 120° C. for one hour in presence of BDMA catalyst. After that, OH-terminated PDMS and dibutyltin dilaurate are added and mixed at 80° C. for another one hour. MHHPA and W12 EST are finally added into the mixture and mechanically stirred to form a mixture. The mixture is degassed at a vacuum oven at 80° C. until no bubble was visible. A varnish obtained is then casted into a mold and cured in the oven according to the following procedures: 2 hours at 100° C., then 2 hours at 120° C., and finally 2 hours at 160° C.

Comparative Example B 20.2 grams (g) of YDH 184 and 6.34 g of aminosilane are first reacted at 120° C. for one hour in presence of 0.13 g of BDMA catalyst. After that, 0.61 g of OH-terminated PDMS and 0.02 g of dibutyltin dilaurate are added and mixed at 80° C. for another one hour to form a mixture. Viscosity of the mixture becomes too high to be stirred. Since the obtained mixture is hard to be degassed completely to get a uniform sample, no further curing is conducted for the Comp Ex B.

TABLE 2

| Raw Materials | Ex 3 | Ex 4 | Ex 5 | Ex 6 | Ex 7 | Ex 8 | Ex 9 | Ex 10 |
|---|---|---|---|---|---|---|---|---|
| YDH 184, wt % | 21.33 | 21 | 20.4 | 19.4 | 21.1 | 21.1 | 21.1 | 20.3 |
| MHHPA, wt % | 18.32 | 18.1 | 17.06 | 15.92 | 18.1 | 18.1 | 18.09 | 15.76 |
| BDMA, wt % | 0.134 | 0.14 | 0.13 | 0.12 | 0.14 | 0.14 | 0.127 | 0.13 |
| OH-terminated PDMS (MW = 4200 g/mol), wt % | 0.21 | 0.63 | 2.04 | 3.88 | 0.63 | 0.63 | 0.63 | 0.61 |
| KH 550, wt % | 0.036 | 0.11 | 0.35 | 0.66 | 0.007 | 0.011 | 0.033 | 3.18 |
| Dibutyltin Dilaurate, wt % | 0.02 | 0.02 | 0.02 | 0.02 | 0.023 | 0.019 | 0.02 | 0.02 |
| W12 EST, wt % | 60 | 60 | 60 | 60 | 60 | 60 | 60 | 60 |
| Total, wt % | 100 | 100 | 100 | 100 | 100 | 100 | 100 | 100 |
| Weight ratio (OH-terminated PDMS/Epoxy resin) | 1% | 3% | 10% | 20% | 3% | 3% | 3% | 3% |
| Molar ratio (—OH/alkoxy group) | 0.17 | 0.17 | 0.17 | 0.17 | 3.33 | 2.00 | 0.67 | 0.007 |

Cured epoxy compositions of Exs 3-5 have very smooth surface with no flowing oil. The surface contact angle with deionized water of Exs 3-5 is 108°, 110° and 111°, respectively, which indicates that the cured epoxy compositions of the invention have hydrophobic surface. In particular, the epoxy composition at a low weight ratio (OH-terminated PDMS/epoxy resin) of 1% provides a surface contact angle with deionized water of 108°.

When the weight ratio of OH-terminated PDMS to the epoxy resin is 20%, cured epoxy composition shows slightly greasy surface, but surface contact angle with deionized water is as high as 115° (Ex 6). In Exs 7 and 8, oily surface is observed. Surface contact angle with deionized water (after cleaning the surface by acetone) of Exs 7 and 8 is 90° and 95°, respectively, which is higher than that of the Comp Ex A. Cured epoxy compositions of Exs 9 and 10 show a uniform surface as in Ex 4. Surface contact angle with deionized water for Exs 9 and 10 is 108° and 110°, respectively.

In contrast, when molar ratio of amine functionality in the aminosilane to the epoxy group in the epoxy resin is 0.26 (Comp Ex B), the viscosity of the reaction product of the epoxy resin, OH-terminated PDMS and aminosilane is too high to be processed.

Properties of the cured epoxy composition of Ex 4 are shown in Table 3. It shows that the cured epoxy composition of the invention has sufficient tracking resistance to pass the 1A3.5 test according to IEC 60587, without compromising mechanical properties of the epoxy composition.

TABLE 3

| Thermal properties | |
| --- | --- |
| $T_g$, °C. | 110 |
| $T_d$, °C. | 340 |
| Mechanical properties | |
| Tensile Strength, Megapascal (MPa) | 75 |
| Elongation at break, % | 1.2 |
| Flexural Strength, MPa | 125 |
| Flexural Strain, % | 1.3 |
| Water pick up (10 days @23 °C.), % | 0.13 |
| Electrical properties | |
| Tracking resistance | Pass 1A3.5 |
| Arcing resistance, second | 184 |
| Surface resistance @ 25° C., Omega (Ω) | $1.55*10^{14}$ |
| Volume resistivity @ 25 °C., Omega · centimeter (Ω · cm) | $3.1*10^{15}$ |
| Electric breakdown strength, kV/mm | >40 |

Examples 11-12

Based on formulations shown in Table 4, epoxy compositions in Exs 11-12 are prepared as in Example 4 except that OH-terminated PDMS with different molecular weight are used.

When using OH-terminated PDMS with molecular weight of 1600 g/mol, surface contact angle with deionized water of the cured epoxy composition is around 110° (Ex 11). When the molecular weight of OH-terminated PDMS is 63,000 g/mol (Ex 12), surface of the cured epoxy composition is slightly greasy. After cleaning the surface of the Ex 12 by acetone, surface contact angle with deionized water is measured to be as high as 110°, which indicates the PDMS chains are chemically bonded into the network of the cured epoxy composition.

Example 13

Based on formulations shown in Table 4 (wt % values are relative to total formulation weight), YDH 184, OH-terminated PDMS (MW=4200 g/mol) and epoxy silane (KH 560) are first mixed at 80° C. for 0.5 hour in presence of dibutyltin dilaurate. After that, MHHPA hardener, BDMA curing catalyst and W12 EST filler are added and mechanically stirred to form a mixture. The mixture is degassed at a vacuum oven at 80° C. until no bubble is observed. A varnish obtained is then casted into a mold and cured in the oven according to the following procedure: 2 hours at 100° C., then 2 hours at 120° C. and finally 2 hours at 160° C.

The surface of the cured epoxy composition is smooth and no flowing oil, and hydrophobic as indicated by a surface contact angle with deionized water of 108°.

TABLE 4

| Raw Materials | Ex 11 | Ex 12 | Ex 13 |
| --- | --- | --- | --- |
| YDH 184, wt % | 21 | 21 | 21.1 |
| MHHPA, wt % | 18 | 18 | 18.1 |
| BDMA, wt % | 0.14 | 0.14 | 0.13 |
| OH-terminated PDMS (MW = 1600 g/mol), wt % | 0.63 | | |
| OH-terminated PDMS (MW = 63,000 g/mol), wt % | | 0.63 | |
| OH-terminated PDMS (MW = 4200 g/mol), wt % | | | 0.45 |
| KH 550, wt % | 0.11 | 0.11 | |
| KH 560, wt % | | | 0.08 |
| Dibutyltin Dilaurate, wt % | 0.02 | 0.02 | 0.02 |
| W12 EST, wt % | 60 | 60 | 60 |
| Total, wt % | 100 | 100 | 100 |

Example 14

21 wt % of YDH 184 and 0.11 wt % aminosilane are first reacted at 80° C. for 4 hours in presence of 0.07 wt % of BDMA catalyst. After that, 0.60 wt % of OH-terminated PDMS (MW=4200 g/mol), 0.20 wt % of decamethylcyclopentasiloxane and 0.02 wt % of dibutyltin dilaurate are added and mixed at 80° C. for another one hour. 18.0 wt % of MHHPA and 60 wt % of W12 EST are finally added and mechanically stirred and forms a mixture. Total weight percent of all the above components is 100%. The mixture is degassed at a vacuum oven at 80° C. until no bubble is observed. A varnish obtained is then casted into a mold and cured in the oven according to the following procedure: 2 hours at 100° C., then 2 hours at 120° C., and finally 2 hours at 160° C.

Hydrophobicity transfer effect test and hydrophobic recovery effect test of the cured epoxy composition (Ex 14) are conducted.

To evaluate the hydrophobicity transfer effect, quartz powder is artificially applied 1.5 to the surface of a specimen forming a 0.4 mm quartz layer (which is actually hydrophilic). In order to test whether or not the specimen can transfer the hydrophobicity to the quartz layer after certain period of time, a 30 microliter (ul) water droplet is applied to the quartz layer using a pipette after the surface is coated for 50 hours, after the surface is coated for 500 hours, respectively. The behavior of the water droplet is observed in three states of the specimen: 1) The specimen is placed in level when the water droplet is applied; 2) The specimen is inclined at 45° when the water droplet is applied; 3) The specimen is initially placed in level when the water droplet is applied, then is declined at 45° after the water droplet is applied. Based on the behavior of the water droplet on the surface of the specimen, hydrophobicity transfer effect is classified into 1, 1.5, 2, 2.5, 3, 3.5, 4, 4.5, 5, respectively, as shown in Table 5. Higher classification number means better hydrophobicity transfer effect.

The classification of hydrophobicity transfer effect is one just after the surface is coated with the quartz powder. Surface of the crosslinked epoxy composition of the invention has a classification of hydrophobicity transfer effect of 3.5 only after being coated with the quartz powder for 50 hours, and a classification of 4 after being coated with the quartz powder for 500 hours. It indicates that the crosslinked epoxy composition has hydrophobicity transfer effect.

TABLE 5

Transfer state system

| Hydrophobic transfer classification | Level specimen | Specimen inclined at 45° | Specimen initially level, then inclined at 45° |
|---|---|---|---|
| 1 | Droplet is immediately absorbed | | |
| 1.5 | Droplet is absorbed within 2 minutes | | |
| 2 | Droplet remains stable for 2 minutes | | |
| 2.5 | | Droplet forms "nose shape" | |
| 3 | | Runs off with a large amount of foreign layer material | Droplet remains stable on tilting |
| 3.5 | | Runs off with a large amount of foreign layer material | Droplet forms "nose shape" on tilting |
| 4 | | | Droplet runs off on tilting leaving a clearly visible track |
| 4.5 | | | Droplet leaves a slight track on tilting |
| 5 | Droplet runs off without foreign material and "dances about" when specimen is tilted slightly | | |

*1-No hydrophobicity transfer effect (THE);
1.5-Between no THE and weak THE;
2-Weak THE;
2.5-Between weak THE and moderate THE;
3-Moderate THE;
3.5-Between moderate THE and good THE;
4-Good THE;
4.5-Between good THE and excellent THE;
5-Excellent THE.

Hydrophobic recovery effect is evaluated by exposing a specimen to oxygen plasma for 2 minutes under gas pressure of 38 Pascal and output of 200 Watt, then the specimen is removed from the oxygen plasma. Surface contact angle with deionized water is measured 6 hours after plasma treatment, 24 hours after plasma treatment, respectively.

Surface contact angle with deionized water of the crosslinked epoxy composition of Ex 13 is 108° before plasma treatment. Six hours after plasma treatment, surface contact angle with deionized water is 87°. Twenty four hours after plasma treatment, surface contact angle with deionized water recovers to 99°, which indicates that the invention provides excellent hydrophobic recovery effect.

The invention claimed is:

1. An epoxy composition comprising:
   (a) an epoxy resin containing at least one epoxy group,
   (b) an anhydride hardener,
   (c) a hydroxyl-terminated polysiloxane, and
   (d) a functional silane having at least one functional group selected from the group consisting of an epoxy-reactive group, an anhydride-reactive group, and an epoxy- and anhydride-reactive group, wherein molar ratio of the functional group of the functional silane to the epoxy group of the epoxy resin (a) is less than 0.25;
   wherein molar ratio of total hydroxyl group(s) in the hydroxyl-terminated polysiloxane to total alkoxy group(s) in the functional silane is 3.5 or less.

2. The epoxy composition of claim 1, wherein the epoxy resin is a cycloaliphatic epoxy resin.

3. The epoxy composition of claim 1, wherein the molar ratio of total hydroxyl group(s) in the hydroxyl-terminated polysiloxane to total alkoxy group(s) in the functional silane is from 0.001 to 1.5.

4. The epoxy composition of claim 1, wherein the functional silane is selected from an aminosilane and an epoxy silane.

5. The epoxy composition of claim 1, wherein the hydroxyl-terminated polysiloxane is hydroxyl-terminated polydimethylsiloxane.

6. The epoxy composition of claim 1, wherein the content of the hydroxyl-terminated polysiloxane is from 0.5 to 25 weight-percent based on the weight of the epoxy resin.

7. The epoxy composition of claim 1, wherein molecular weight of the hydroxyl-terminated polysiloxane is from 400 grams per mole to 70,000 grams per mole.

8. The epoxy composition of claim 1 further comprising a cyclic polysiloxane.

9. The epoxy composition of claim 8, wherein the content of the cyclic polysiloxane is from one to 3 weight-percent, based on the epoxy resin weight.

10. A crosslinked epoxy composition obtained by curing the epoxy composition of any of claims 1-9.

11. A method for preparing the epoxy composition of claim 1, comprising steps of mixing
   (a) an epoxy resin containing at least one epoxy group,
   (b) an anhydride hardener,
   (c) a hydroxyl-terminated polysiloxane, and
   (d) a functional silane having at least one functional group selected from the group consisting of an epoxy-reactive group, an anhydride-reactive group, and an epoxy- and anhydride-reactive group, wherein molar ratio of the functional group of the functional silane to the epoxy group of the epoxy resin (a) is less than 0.25;
   wherein molar ratio of total hydroxyl group(s) in the hydroxyl-terminated polysiloxane to total alkoxy group(s) in the functional silane is 3.5 or less.

12. The method of claim 11, wherein the anhydride hardener, the hydroxyl-terminated polysiloxane and the functional silane are mixed to react first, before mixing with the epoxy resin.

13. The method of claim 11, wherein the epoxy resin, the hydroxyl-terminated polysiloxane and the functional silane are mixed to react first, before mixing with the anhydride hardener.

14. The method of claim 13, wherein the epoxy resin reacts with the functional silane having at least one epoxy-reactive group or at least one epoxy- and anhydride-reactive group first, before mixing with the hydroxyl-terminated polysiloxane.

* * * * *